United States Patent
Kanno et al.

(10) Patent No.: US 8,956,156 B2
(45) Date of Patent: Feb. 17, 2015

(54) DEVICE FOR TREATING PERI-IMPLANTITIS

(71) Applicant: A-Z Ltd., Sendai-shi, Miyagi (JP)

(72) Inventors: Taro Kanno, Sendai (JP); Keisuke Nakamura, Sendai (JP); Yoshimi Niwano, Osakasayama (JP); Minoru Kanno, Sendai (JP)

(73) Assignee: A-Z Ltd., Miyagi (JP)

( * ) Notice: Subject to any disclaimer, the term of this patent is extended or adjusted under 35 U.S.C. 154(b) by 0 days.

(21) Appl. No.: 14/134,500

(22) Filed: Dec. 19, 2013

(65) Prior Publication Data

US 2014/0255869 A1    Sep. 11, 2014

Related U.S. Application Data

(60) Provisional application No. 61/774,842, filed on Mar. 8, 2013.

(51) Int. Cl.

| | |
|---|---|
| *A61C 1/00* | (2006.01) |
| *A61L 2/08* | (2006.01) |
| *A61C 17/22* | (2006.01) |
| *A61L 2/10* | (2006.01) |
| *A61L 2/18* | (2006.01) |

(52) U.S. Cl.
CPC . *A61L 2/08* (2013.01); *A61C 17/22* (2013.01); *A61L 2/084* (2013.01); *A61L 2/10* (2013.01); *A61L 2/186* (2013.01); *A61L 2/183* (2013.01)
USPC .......................................... 433/29

(58) Field of Classification Search
USPC ...................................... 433/26, 29, 172–176
See application file for complete search history.

(56) References Cited

U.S. PATENT DOCUMENTS

| | | | |
|---|---|---|---|
| 2006/0085052 | A1 | 4/2006 | Feuerstein et al. |
| 2010/0233645 | A1* | 9/2010 | Rizoiu ............................ 433/29 |

FOREIGN PATENT DOCUMENTS

| | | |
|---|---|---|
| JP | 2007-508065 | 4/2007 |
| JP | 2007-135794 | 6/2007 |
| JP | 2008-080102 | 4/2008 |
| JP | 2010-518961 | 6/2010 |
| JP | 2012-282607 | 12/2012 |
| WO | WO 2012/098772 | 7/2012 |

OTHER PUBLICATIONS

International Search Report dated Oct. 2, 2012 from International Patent Application No. PCT/JP2013/056449 (3 pages).

* cited by examiner

*Primary Examiner* — Sunil K Singh
(74) *Attorney, Agent, or Firm* — Harness, Dickey & Pierce, P.L.C.

(57) ABSTRACT

A device includes: a cylindrical first main body having a bottom surface, an inner side surface, and an outer side surface, the first main body having at least one electromagnetic wave irradiation port and at least one antiseptic discharge port, the at least one electromagnetic wave irradiation port being provided in the inner side surface of the first main body, the at least one antiseptic discharge port being provided in the bottom surface and/or the inner side surface of the first main body; an electromagnetic wave generation source; and an antiseptic supply source.

8 Claims, 6 Drawing Sheets

DEVICE FOR TREATING PERI-IMPLANTITIS

CROSS-REFERENCE TO RELATED APPLICATIONS

This application claims the benefit of U.S. Provisional Application No. 61/774,842, filed on Mar. 8, 2013, the entire disclosure of which is incorporated herein by reference.

TECHNICAL FIELD

The present invention relates to a device for treating peri-implantitis, and particularly relates to a device including: a cylindrical first main body having a device bottom surface, an inner side surface, and an outer side surface around an implant, the first main body having at least one electromagnetic wave irradiation port and at least one antiseptic discharge port, the at least one electromagnetic wave irradiation port being provided in the inner side surface of the first main body, the at least one antiseptic discharge port being provided in the bottom surface and/or the inner side surface of the first main body; an electromagnetic wave generation source; and an antiseptic supply source.

BACKGROUND OF THE INVENTION

A dental implant includes: a superstructure A corresponding to a tooth; a fixture B adapted to be buried in a side where a tooth is lost, the fixture B being directly coupled to a bone D and functioning as an artificial tooth root; and an abutment C adapted to attach the superstructure A and the fixture B (see FIG. 1).

JP-A-2010-518961 discloses: a use method in which particles of microstructure are used in preparation of an agent in the form of an injectable suspension containing the particles of microstructure and a fluid vehicle, the particles of microstructure containing titanium, a titanium alloy, at least one type of titanium oxide, or a combination thereof and having a surface with at least a considerable part made of at least one type of titanium oxide; and a use method in which the agent is used for treating an inflammatory and/or bacterial condition selected from the group consisting of periodontitis, peri-implantitis, and osteitis, in which the argent alleviates and/or eliminates the inflammatory and/or bacterial condition, and/or promotes regeneration of tissues in the injected site.

JP-A-2010-518961 discloses a method of treating a condition selected from the group consisting of periodontitis, peri-implantitis, and osteitis, in which an implant having one or both of an anti-inflammatory effect and an antibacterial effect and intended to be injected into a human body or an animal body is brought into contact with a site typical in a condition to be treated, the implant comprising at least one porous grain or granule, in which the at least one porous grain or granule: contains titanium, or one or a plurality of titanium oxides or titanium alloys; has an titanium oxide layer in its surface; has a mean length, from one side to the opposite side through a geometrical center, of up to 5 mm; and has a mean specific surface area of 0.15 m$^2$/g according to the BET method.

Further, WO-2012-098772 discloses a sterilizing device and the like, which are configured to bring an antiseptic containing a catechin or a group of catechins into contact with a subject to be sterilized, and then irradiate the antiseptic with light. Moreover, Japanese Patent Application No. 2012-282607 discloses use of a specific polyphenol for promoting wound healing, a wound-healing promoter containing a specific polyphenol, and a drug composition for wound healing containing a specific polyphenol.

SUMMARY OF THE INVENTION

Technical Problems

However, JP-A-2010-518961 fails to disclose how the agent for treating peri-implantitis is supplied. Similarly, JP-A-2010-518961 fails to disclose how the implant for treating peri-implantitis is brought into contact with peri-implantitis. Furthermore, WO-2012-098772 and Japanese Patent Application No. 2012-282607 fail to disclose a specific sterilizing device, either.

To solve the above-described conventional problems, a main object of the present invention is to provide a device for easily and safely treating peri-implantitis.

Solution to Problems

To achieve the above-described object, the present invention provides a device for treating peri-implantitis having the following characteristics.

Advantageous Effects of Invention

According to a first aspect of the present invention, it is possible to sterilize a fixture of an implant buried in a site where a tooth is lost with electromagnetic wave and antiseptic by covering the fixture of the implant with the device makes it possible to.

According to a second aspect of the present invention, it is possible to sterilize a fixture of an implant buried in a site where a tooth is lost with electromagnetic wave and antiseptic while cleaning a surface of the fixture of the implant by rotating the plurality of brushes.

According to a third aspect of the present invention, it is possible to sterilize a fixture of an implant by photolysis of hydrogen peroxide using hydrogen peroxide or by photolysis of hydrogen peroxide using the antiseptic containing a catechin.

Otherwise, using the polyphenol makes it possible to promote wound healing around a fixture of an implant in the oral cavity and to reduce oxidative stress during inflammation (reactive oxygen species produced by inflammatory cells such as neutrophils), and also to sterilize the fixture of the implant can be sterilized by the electromagnetic wave.

According to a fourth aspect of the present invention, since the electromagnetic wave generation source is a blue LED, even if the human body itself, other than a fixture of an implant, is irradiated with the electromagnetic wave, the irradiation is unlikely to adversely affect the human body. Further, since the electromagnetic wave emitted by the blue LED is a visible light, it is possible to easily recognize that the human body is irradiated with the electromagnetic wave, and to return the device to the fixture of the implant.

According to a fifth aspect of the present invention, since the electromagnetic wave is an ultraviolet ray, the photolysis of hydrogen peroxide sterilization can be further enhanced to increase the sterilizing effect. Further, the irradiation of the ultraviolet ray provides a photocatalytic effect of titanium, and thus, a more powerful sterilizing effect can be expected.

According to a sixth aspect of the present invention, the wavelength of the visible light from the blue LED can be changed depending on the condition of a peri-implantitis, and thus, a device with a high cost performance can be provided.

According to a seventh aspect of the present invention, the wavelength of the ultraviolet ray can be changed depending on the condition of the peri-implantitis, and thus, a device with a high cost performance can be provided.

Other objects, characteristics, and advantages of the present invention will be made clear from the description of embodiments of the present invention regarding the attached drawings.

DESCRIPTION OF THE EMBODIMENTS

Hereinafter, embodiments of the present invention will be described in detail with reference to the attached drawings. Throughout the drawings, the same constituent elements are denoted by the same reference signs.

Figure 1:
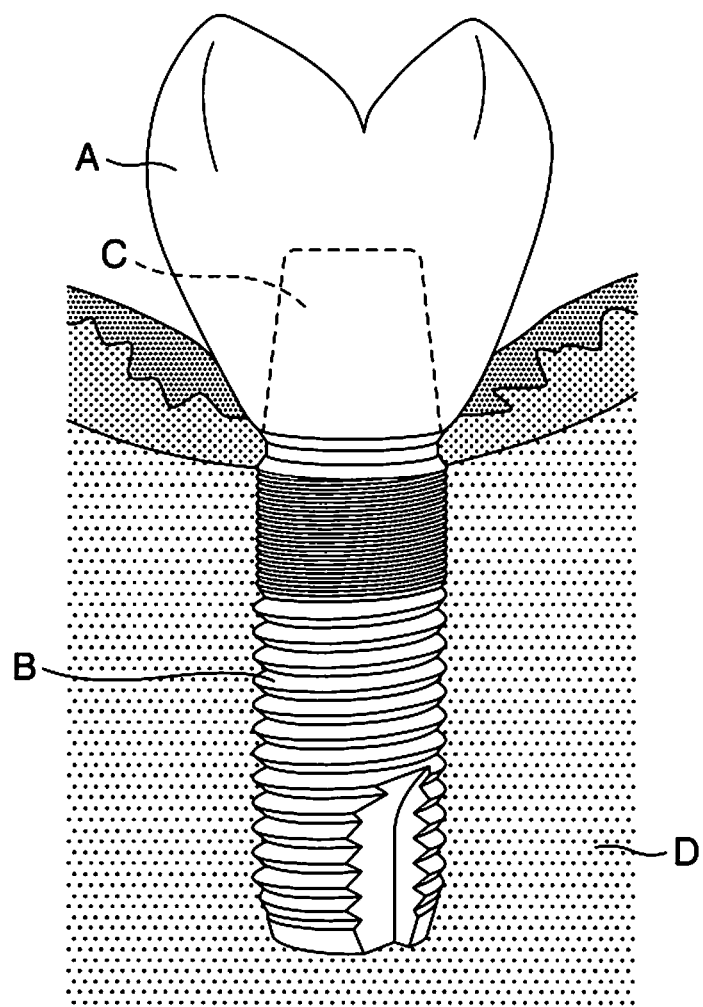
FIG. 1 is a schematic view of a state where a dental implant used in place of a tooth is buried in a site where a tooth is lost.
Figure 2:
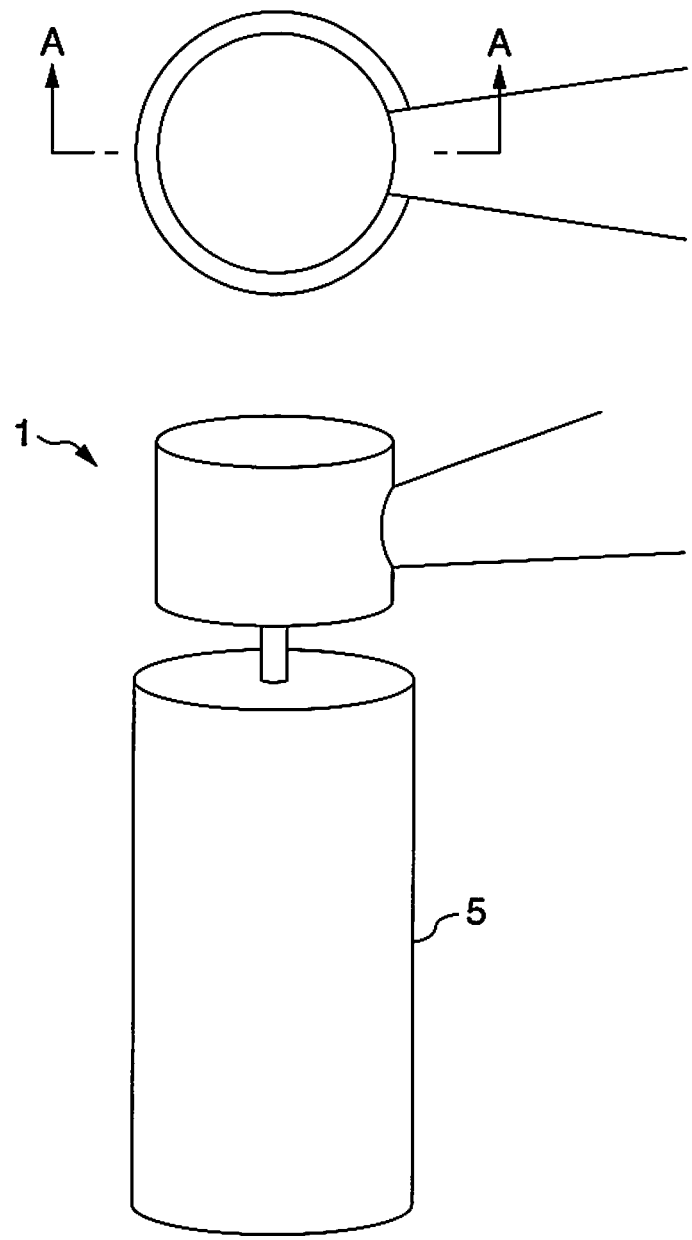
FIG. 2 is a plan view and a schematic perspective view of a device for treating a peri-implantitis according to an embodiment of the invention of the present application.
Figure 3:
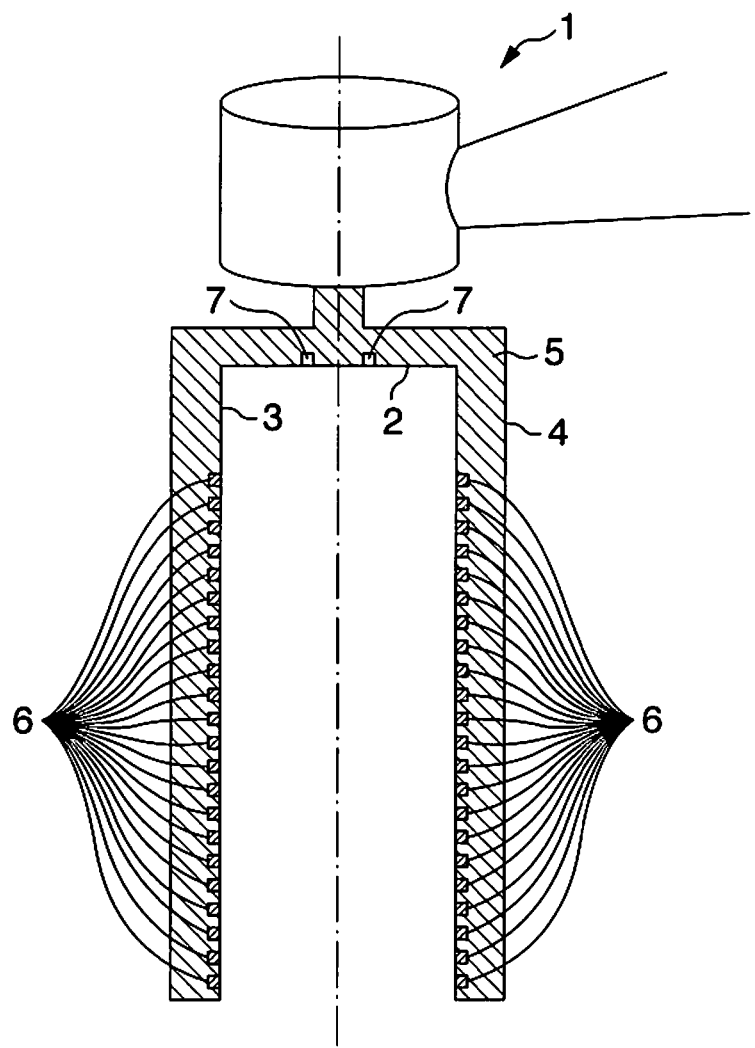
FIG. 3 is a cross-sectional view of a device of one embodiment of the invention of the present application, which is taken along the line A-A in FIG. 2.

Referring to FIGS. 2 and 3, a device 1 for treating peri-implantitis according to one embodiment of the invention of the present application includes: a cylindrical first main body 5 having a bottom surface 2, an inner side surface 3, and an outer side surface 4, the first main body 5 having at least one electromagnetic wave irradiation port 6 provided in the inner side surface 3 of the first main body 5 and at least one antiseptic discharge port 7 provided in the bottom surface 2 and/or the inner side surface 3 of the first main body 5; an unillustrated electromagnetic wave generation source; and an unillustrated antiseptic supply source.

With this configuration, the device 1 is capable of sterilizing a fixture B of an implant buried in a site where a tooth is lost, with an electromagnetic wave and an antiseptic by covering the fixture B of the implant with the device 1.

Here, the implant has a diameter of 10 mm or less and a height of 30 mm or less, and the first main body 5 may have any dimensions as long as the first main body 5 is capable of being employed for the implant with such a size.

Figure 5:
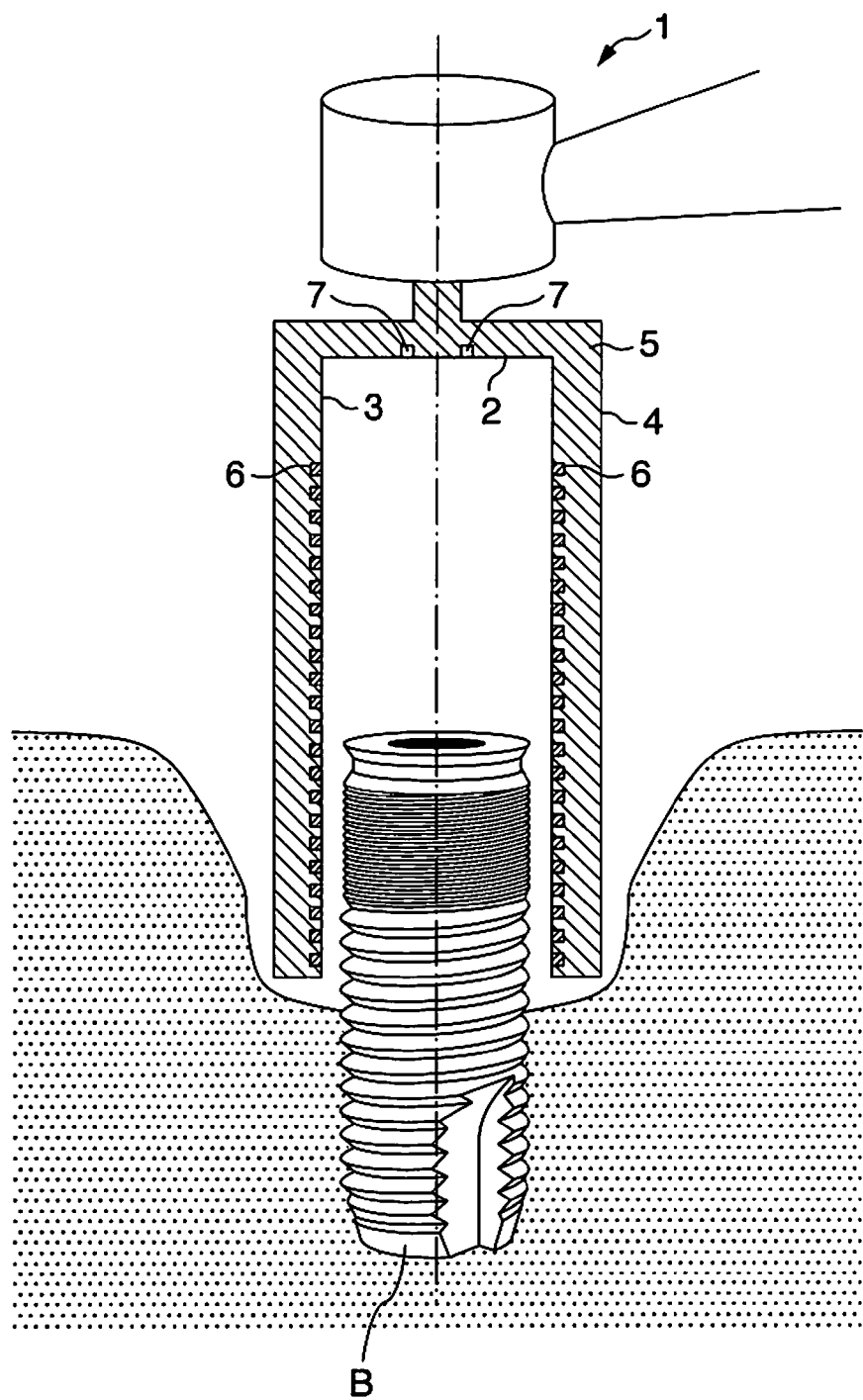
FIG. 5 is a schematic view of a state where a fixture of an implant buried in a site where a tooth is lost is covered with the device of FIG. 3.

The electromagnetic wave generation source and the electromagnetic wave irradiation port 6 are coupled to each other with an optical fiber or the like, and the antiseptic supply source and the antiseptic discharge port 7 are coupled to each other with a tube or the like. As shown in FIG. 5, the fixture B of the implant buried in a site where a tooth is lost is covered with the device 1 for treating peri-implantitis, and in this state, pressing one switch of an unillustrated controller starts the irradiation of the electromagnetic wave and the discharge of the antiseptic. Then, pressing another switch of the controller terminates the irradiation of the electromagnetic wave and the discharge of the antiseptic. Alternatively, the device 1 may be configured such that the irradiation of the electromagnetic wave, the discharge of the antiseptic, and the termination thereof are repeated every time a switch is pressed. Further, the device 1 may be provided with a plurality of switches and configured such that pressing one of the switches activates the irradiation of the electromagnetic wave, and pressing another one of the switches activates the discharge of the antiseptic. In this case, the irradiation of the electromagnetic wave and the discharge of the antiseptic are terminated by combining the above-described switches.

Figure 4:
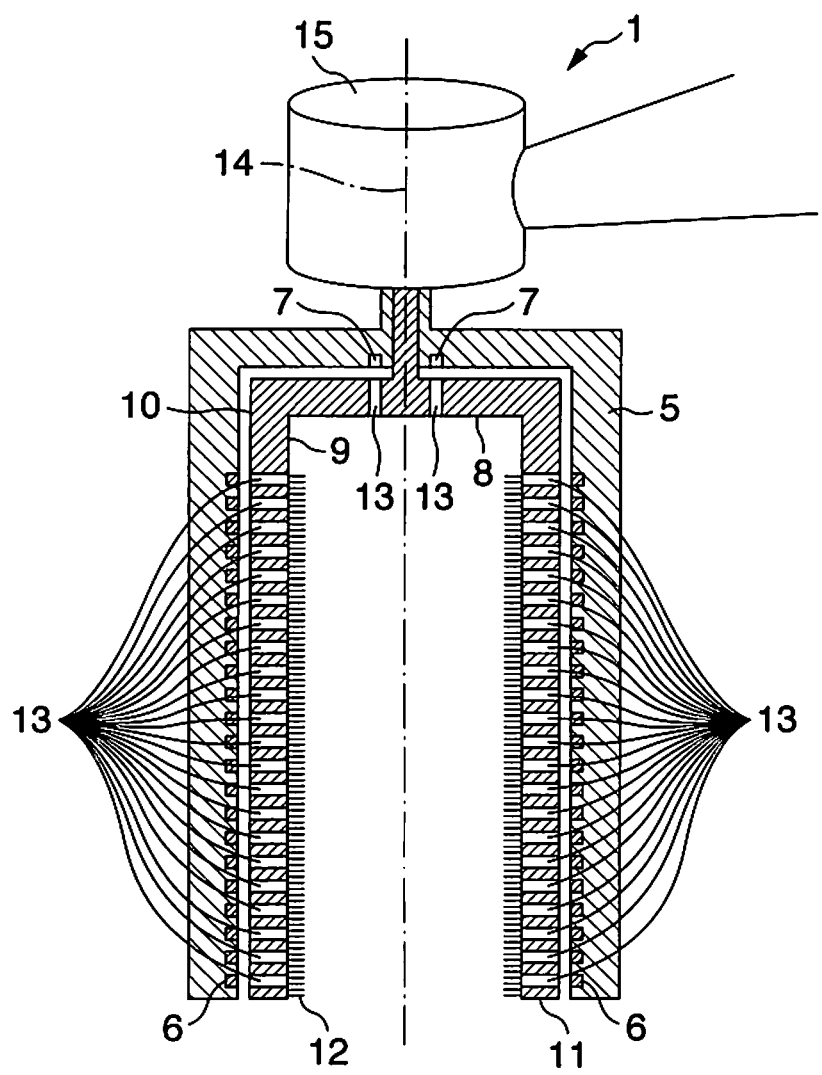
FIG. 4 is a cross-sectional view of a device of another embodiment of the invention of the present application, which is taken along the line A-A in FIG. 2.

Referring to FIGS. 2 and 4, a first main body 5 of a device 1 for treating peri-implantitis according to another embodiment of the invention of the present application includes a cylindrical second main body 11 having a bottom surface 8, an inner side surface 9, and an outer side surface 10, and a plurality of brushes 12 are provided on at least a part of the inner side surface 9 of the second main body 11. Further, at least one through-hole 13 through which the irradiation port 6 or the discharge port 7 communicates with an inner space of the second main body 11 is provided on the bottom surface 8 and/or the inner side surface 9 and the outer side surface 10 of the second main body 11. The device 1 includes a drive unit 15 provided to rotate the second main body 11 about an axis 14 of the second main body 11. The drive unit 15 is typically a motor.

By rotating the plurality of brushes 12, it is possible to sterilize the fixture B of the implant with an electromagnetic wave and an antiseptic while cleaning the surface of the fixture B of the implant.

Here, the implant has a diameter of 10 mm or less and a height of 30 mm or less, and the first main body 5 and the second main body 11 may have any dimensions as long as the first main body 5 and the second main body 11 are capable of being employed for the implant with such a size.

Figure 6:
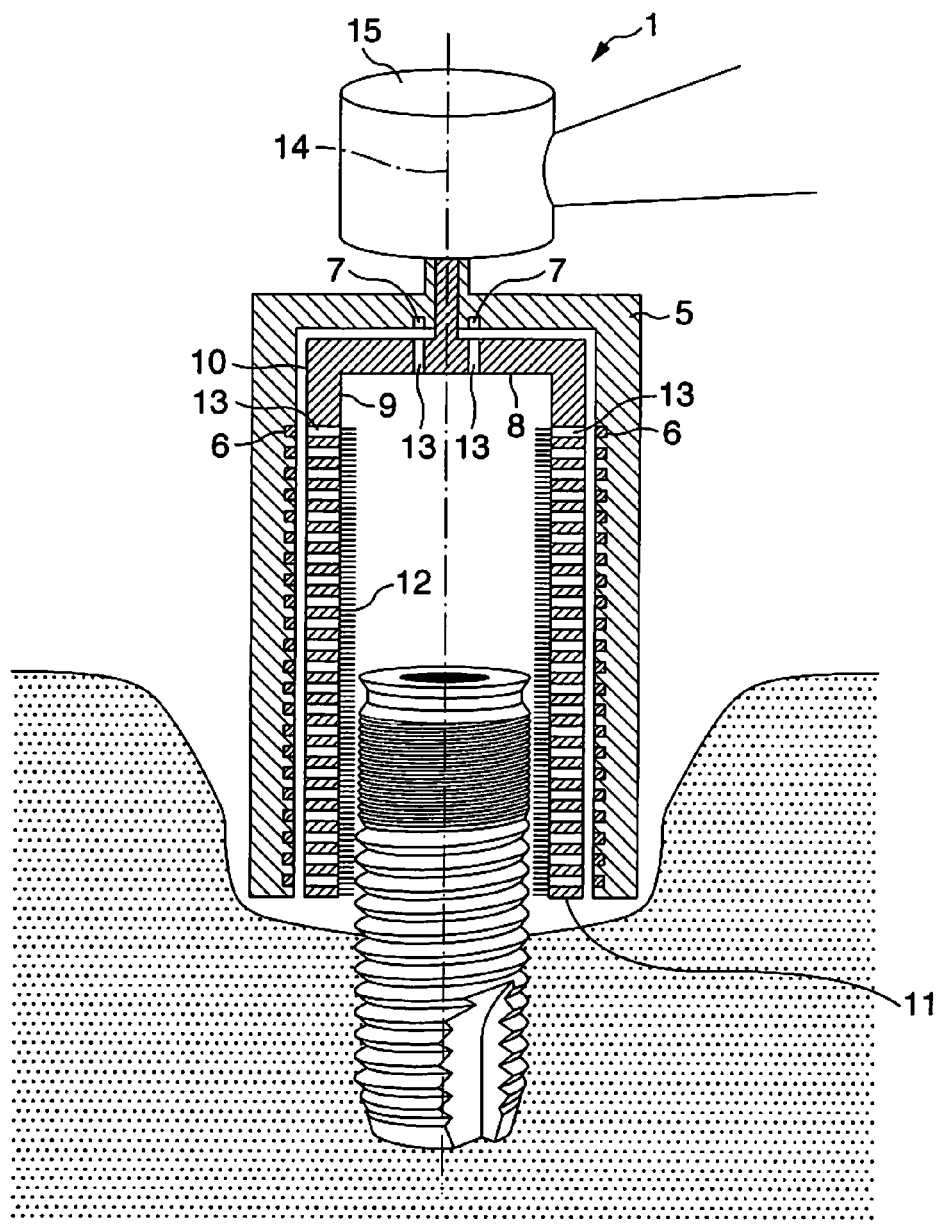
FIG. 6 is a schematic view of a state where a fixture of an implant buried in a site where a tooth is lost is covered with the device of FIG. 4.

Like the one embodiment, the electromagnetic wave generation source and the electromagnetic wave irradiation port 6 are coupled to each other with an optical fiber or the like, and the antiseptic supply source and the antiseptic discharge port 7 are coupled to each other with a tube or the like. As shown in FIG. 6, the fixture B of the implant buried in a site where a tooth is lost is covered with the device 1 for treating peri-implantitis, and in this state, pressing a switch of an unillustrated controller starts the irradiation of the electromagnetic wave and the discharge of the antiseptic, and also drives the drive unit 15 to rotate the second main body 11 about the axis 14 of the second main body 11. Pressing another switch terminates the irradiation of the electromagnetic wave, the discharge of the antiseptic, and the rotation of the second main body 11. Alternatively, the device 1 may be configured such that the irradiation of the electromagnetic wave, the discharge of the antiseptic, the rotation of the second main body 11, and the termination thereof are repeated every time a switch is pressed. Further, the device 1 may be provided with a plurality of switches and configured such that pressing one of the switches activates the irradiation of the electromagnetic wave, pressing another one of the switches activates the discharge of the antiseptic, and pressing still another one of the switches rotate the second main body 11. In this case, the irradiation of the electromagnetic wave, the discharge of the antiseptic, and the rotation of the second main body 11 are terminated by combining the above-described switches.

In addition, in another embodiment, the antiseptic may be selected from hydrogen peroxide, an antiseptic containing a catechin, a group of catechins, and/or a polyphenol solution. With this configuration, the fixture of the implant can be sterilized by photolysis of hydrogen peroxide using hydrogen peroxide or by photolysis of hydrogen peroxide using the antiseptic containing a catechin, a group of catechins and/or a polyphenol compound. Otherwise, using the polyphenol makes it possible to promote wound healing around the fixture of the implant in the oral cavity and to reduce oxidative stress during inflammation (reactive oxygen species produced by inflammatory cells such as neutrophils), and also, the fixture of the implant can be sterilized by the electromagnetic wave.

Moreover, in another embodiment, the electromagnetic wave generation source may be a blue LED. With this configuration, even if the human body itself, other than the fixture B of the implant, is irradiated with the electromagnetic wave, the irradiation is unlikely to adversely affect the human body. Further, since the electromagnetic wave emitted by the blue LED is a visible light, it is possible to easily recognize that the human body is irradiated with the electromagnetic wave, and to return the device to the fixture B of the implant.

In yet another embodiment, the electromagnetic wave may be an ultraviolet ray. With this configuration, the photolysis of hydrogen peroxide sterilization can be further enhanced to increase the sterilizing effect. Further, the irradiation of the ultraviolet ray provides a photocatalytic effect of titanium, and thus, a more powerful sterilizing effect can be expected.

In still another embodiment, the wavelength of the visible light of the blue LED may be in a range from 400 to 500 nm. With this configuration, the wavelength of the visible light from the blue LED can be changed depending on the condition of the peri-implantitis, and thus, a device with a high cost performance can be provided. In this case, the controller may be provided with a display unit for displaying the current wavelength or may be provided with a slide switch for changing the wavelength. What is important here is that any type of a switch may be used as long as the switch is capable of changing the wavelength.

Furthermore, in another embodiment, the wavelength of the ultraviolet ray may be in a range from 200 to 399 nm. With this configuration, the wavelength of the ultraviolet ray can be changed depending on the condition of the peri-implantitis, and thus, a device with a high cost performance can be provided. In this case as well, the controller may be provided with a display unit for displaying the current wavelength or may be provided with a slide switch for changing the wavelength. What is important here is that any type of a switch may be used as long as the switch is capable of changing the wavelength.

Here, the device 1 of the invention of the present application may have both an electromagnetic wave generation source for irradiation of an ultraviolet ray and a blue LED as the electromagnetic wave generation source. With this configuration, the ultraviolet ray or the visible light can be irradiated depending on the condition of the peri-implantitis. The range of the wavelength of the ultraviolet ray or the visible light in this case is from 200 to 500 nm.

Although the above description has been given of the embodiments, the present invention is not limited to these embodiments, and it is apparent to those skilled in the art that various modifications and change may be made without departing from the spirit of the present invention and the scope of the attached claims.

REFERENCE SIGNS LIST 1 device for treating peri-implantitis
2 bottom surface
3 inner side surface
4 outer side surface
5 first main body
6 electromagnetic wave irradiation port
7 antiseptic discharge port
8 bottom surface
9 inner side surface
10 outer side surface
11 second main body
12 brush
13 through-hole
14 axis of second main body
15 drive unit

The invention claimed is:

1. A device for treating peri-implantitis, comprising:
a cylindrical first main body having a bottom surface, an inner side surface, and an outer side surface, the first main body having at least one electromagnetic wave irradiation port and at least one antiseptic discharge port, the at least one electromagnetic wave irradiation port being provided in the inner side surface of the first main body, the at least one antiseptic discharge port being provided in the bottom surface and/or the inner side surface of the first main body;
an electromagnetic wave generation source; and
an antiseptic supply source; wherein
the first main body has a cylindrical second main body inside the first main body, the second main body having a bottom surface, an inner side surface, and an outer side surface,
a plurality of brushes are provided on at least a part of the inner side surface of the second main body,
at least one through-hole through which the irradiation port or the discharge port communicates with an inner space of the second main body is provided on the bottom surface and/or the inner side surface and the outer side surface of the second main body, and
the device comprises a drive unit provided to rotate the second main body about an axis of the second main body.

2. The device according to claim 1, wherein the antiseptic is selected from hydrogen peroxide, an antiseptic containing a catechin, and a polyphenol solution.

3. The device according to claim 1, wherein the electromagnetic wave generation source is a blue LED.

4. The device according to claim 2, wherein the electromagnetic wave generation source is a blue LED.

5. The device according to claim 1, wherein the electromagnetic wave is an ultraviolet ray.

6. The device according to claim 2, wherein the electromagnetic wave is an ultraviolet ray.

7. The device according to claim 3, wherein a wavelength of a visible light of the blue LED is in a range from 400 to 500 nm.

8. The device according to claim 5, wherein a wavelength of the ultraviolet ray is in a range from 200 to 399 nm.

* * * * *